(12) United States Patent
Duckert

(10) Patent No.: US 6,389,312 B1
(45) Date of Patent: May 14, 2002

(54) METHOD AND SYSTEM HAVING SIMPLIFIED NEUROMUSCULAR TRANSMISSION SCORING

(75) Inventor: David Wayne Duckert, Menomonee Falls, WI (US)

(73) Assignee: General Electric Company, Milwaukee, WI (US)

( * ) Notice: Subject to any disclaimer, the term of this patent is extended or adjusted under 35 U.S.C. 154(b) by 49 days.

(21) Appl. No.: 09/628,989

(22) Filed: Jul. 21, 2000

(51) Int. Cl.[7] .............................................. A61B 5/04
(52) U.S. Cl. ..................................................... 600/546
(58) Field of Search ................................ 600/546, 547, 600/554, 595; 434/262, 265, 267; 604/246; 128/DIG. 13

(56) References Cited

U.S. PATENT DOCUMENTS 4,387,723 A * 6/1983 Atlee, III et al. ............ 600/547
5,256,156 A * 10/1993 Kern et al. .................. 604/246
5,391,081 A * 2/1995 Lampotang et al. ........ 434/262
5,957,860 A * 9/1999 Rodiera Olive ............. 600/546

* cited by examiner

Primary Examiner—Kevin Shaver
Assistant Examiner—Brian Szmal
(74) Attorney, Agent, or Firm—Timothy J. Ziolkowski; Peter J. Vogel; Cook & Franke SC

(57) ABSTRACT

A method and apparatus are each disclosed that are capable of providing a simplified neuromuscular transmission score utilizing multiple conventional stimulus modes. After applying a neuromuscular stimuli to a patient and measuring a neuromuscular response from the patient, a universal value is assigned to the neuromuscular response signal. The universal value is applicable to a single progressive scale that encompasses the multiple conventional stimulus mode scales. A neuromuscular transmission monitor is disclosed having at least one electrode, a transducer, and a processing unit to process the data and determine a correct stimulus mode for the neuromuscular response signal and produce a non-mode specific value applicable to the single universal scale. The technique is implemented in a computer program which may reside in the memory of either the neuromuscular transmission monitor, or a host patient monitor. In the former, the neuromuscular transmission monitor is more autonomous, and in the latter, acts more of a slave unit.

27 Claims, 2 Drawing Sheets

METHOD AND SYSTEM HAVING SIMPLIFIED NEUROMUSCULAR TRANSMISSION SCORING

BACKGROUND OF THE INVENTION

The present invention relates generally to medical devices, and more particularly to, a neuromuscular transmission monitor simplified scoring and a method of neuromuscular transmission scoring.

Neuromuscular monitoring is the measurement of the neuromuscular transmission of a patient. Before surgery, anesthesia is administered to the patient. A part of anesthesia is the administration of a neuromuscular blocking agent. This agent is used to block neuromuscular activity and paralyze the muscles of the body to allow intubation and/or to facilitate the surgical procedure. Intubation is the process of placing a tube into the patient's trachea to establish an airway. The tube is connected to a ventilator which effectively breathes for the patient. Inserting the tube requires that the muscles of the throat, diaphragm, and larynx must be paralyzed. Without this paralyzing effect, reflexes would make the insertion of the tube difficult and problematic.

Additionally, certain surgical procedures are extremely delicate and must be performed under a microscope. In such cases, any patient movement could be disastrous to the outcome of the procedure. Coughing, bucking, or any reflex movement due to the irritation caused by the tube, for example, is a common occurrence in unblocked, or unparalyzed patients. To eliminate all movement, a large dose of neuromuscular blocking agent is given to completely paralyze the patient. Further, abdominal cases generally require the patient's muscle tone be totally abolished to facilitate the surgical procedure.

At the end of a surgical procedure, the neuromuscular block must be reversed and neuromuscular activity must be returned to normal to ensure the patient is able to breathe unassisted before the ventilator and tube are removed. As is evident then, it is necessary to measure neuromuscular response and effectively assess those results. The measurement of neuromuscular transmission generally involves electrically stimulating a nerve fiber and measuring the physical response of the associated muscle. Typically, the stimulation occurs at the ulnar nerve near the wrist. In response, the adductor pollicis, near the thumb, moves responsively. Depending on the amount of blocking agent administered, different degrees of neuromuscular block can be achieved.

Some cases require very little paralyzation, while others require long periods of intense block. After applying a small electrical current to the patient's skin near the ulnar nerve, the response of the muscle in the thumb is recorded. With a deep block, the thumb may not move at all. With no block, the thumb's movement is quite pronounced. With a shallow block, the thumb's movement is somewhere therebetween. A trained anesthesiologist can gauge the thumb movement by feel and adjust the administration of the drug accordingly. While this method is quite effective for a trained anesthesiologist, it is dependent on the anesthesiologist's skill level and provides no quantitative recorded data.

The use of neuromuscular transmission monitors to measure neuromuscular transmission results in a wide dynamic range in which the complete spectrum is comprised of three segments, each segment having a unique set of parameters applicable to its own scale. The least sensitive segment is the Train-of-Four (TOF). In this technique, a constant current waveform of four pulses is applied. This method allows determination of the block depth to be made independent of the absolute response amplitude. The absolute amplitude can vary with temperature, arm position, stimulus current and other variables. The response in the TOF technique is four muscular movements corresponding to the four stimulus pulses. The ratio of the fourth response amplitude to the first response amplitude is the TOF ratio. This scale ranges from 0 to 100% and is used when the patient is lightly blocked or during recovery from neuromuscular block. The next segment, or scale, is the Twitch Count (TC) which is a medium sensitivity segment used where there is a moderate degree of paralyzation. The Twitch Count is the actual number of responses from a series of four pulses. The Twitch Count can range from 1 up to 4. The most sensitive segment is the Post-Tetanic Count (PTC) and is measured using a more aggressive stimulus. This method applies a more intense stimulus to the nerve to produce a condition of tetany in the corresponding muscle. This has the effect of sensitizing the neuromuscular junction. Immediately following this intense stimulus, a periodic stimulus is delivered. The number of responses to the periodic stimulus is the PTC value. The PTC value can range from 0 up to 20. A fourth neuromuscular transmission mode is sometimes used in critical situations. This mode measures the normalized twitch amplitude rapidly to determine when intubation is possible.

Each of these various different scales can be used during a typical case to measure neuromuscular transmission response of a patient. Since the values are not progressive and since there is some overlap between the scales, they are not well understood by most clinicians. This results in general confusion about these scales, their readings, and how they relate to one another. For example, it is not obvious that a patient with a PTC of 5 is more blocked than a patient with a Twitch Count of 3, or that a patient with a TOF ratio of 50% is less blocked than one with a Twitch Count of 1.

The problem is best described with an analogy to an automobile having three speedometers ranges. One will readily recognize the confusion to most automobile operators if one speedometer, meant for low speeds, reports the speed in feet per second, while a second speedometer, meant for moderate speeds, reports the speed in kilometers per hour, and a third speedometer, designed for high speeds, reports the speed in miles per hour. Assume further that the driver must know which speedometer to choose at any given time and if he is to maintain his speed at a given limit, the driver may have to make a units conversion "on the fly".

During neuromuscular monitoring of a patient under anesthesia, it is-also sometimes important to the anesthesiologist to trend the amount of blocking at given times. Having three different scales of measurement makes it very difficult to trend from anesthesia administration, through surgery, and through the administration of reversal agents.

It is therefore evident that there is a need for a simplified neuromuscular transmission scoring system.

SUMMARY OF THE INVENTION

The present invention includes a method and apparatus that incorporates a simplified neuromuscular transmission scoring system that solves the aforementioned problems.

The present invention consolidates the multiple, different scales of measurement for neuromuscular transmission scores into a single universal continuum. In addition, the monitor is capable of determining the appropriate mode of operation. The invention includes the implementation of a simple, single scale to measure neuromuscular transmission.

The measuring device applies the correct stimuli and acceptable techniques to measure the TOF ratio, the Twitch Count, and the PTC. The measured data is converted into a single scale or neuromuscular universal score. The single universal scale is easy to learn, use, and display trending. The complexity of the multiple different conventional scales then need not be revealed to the clinician to avoid confusion.

In accordance with one aspect of the invention, a method of neuromuscular (NM) transmission scoring includes applying a NM stimuli to a patient, measuring a NM response from the patient, and assigning a universal value of the NM response to a single progressive scale that encompasses at least 2 stimulus modes, each of the stimulus modes having a unique scale and parameter definition.

In accordance with another aspect of the invention, a method of converting neuromuscular transmission measurement scales to a single progressive scale, additionally includes determining which one of the at least 2 different scales the neuromuscular response belongs thereto, and then assigning a value of the neuromuscular response within the one of the at least 2 different scales. The assigned value is then converted to the single progressive scale encompassing each of the at least 2 different scales.

In accordance with another aspect of the invention, a computer program is disclosed that resides on a computer readable memory capable of causing a processor, when executed, to receive an NM response value that is in one of at least two different formats and then determine which one of the at least two different formats the NM response value is in. The computer program then converts the NM response value to a universal value applicable to a single scale encompassing each of the different formats.

In accordance with yet another aspect of the invention, a neuromuscular transmission monitor is disclosed that has at least one patient electrode to stimulate a muscle of a patient and a transducer to measure an NM response to the muscle stimuli and create a NM response signal therefrom. A power supply is connected to the patient electrodes to supply muscle stimulating power to the patient electrode. A processing unit is connected to the patient electrode and a transducer to control the muscle stimulating power to the patient electrode and process the neuromuscular response signal from the transducer. The processing unit is further programmed to determine a correct stimulus mode for the neuromuscular response signal and produce a non-mode specific value applicable to a single scale that encompasses multiple stimulus modes based on the determined stimulus mode and the neuromuscular response signal.

Various other features, objects and advantages of the present invention will be made apparent from the following detailed description and the drawings.

BRIEF DESCRIPTION OF THE DRAWINGS

The drawings illustrate the best mode presently contemplated for carrying out the invention.

In the drawings.

DETAILED DESCRIPTION OF THE PREFERRED EMBODIMENT

Figure 1:
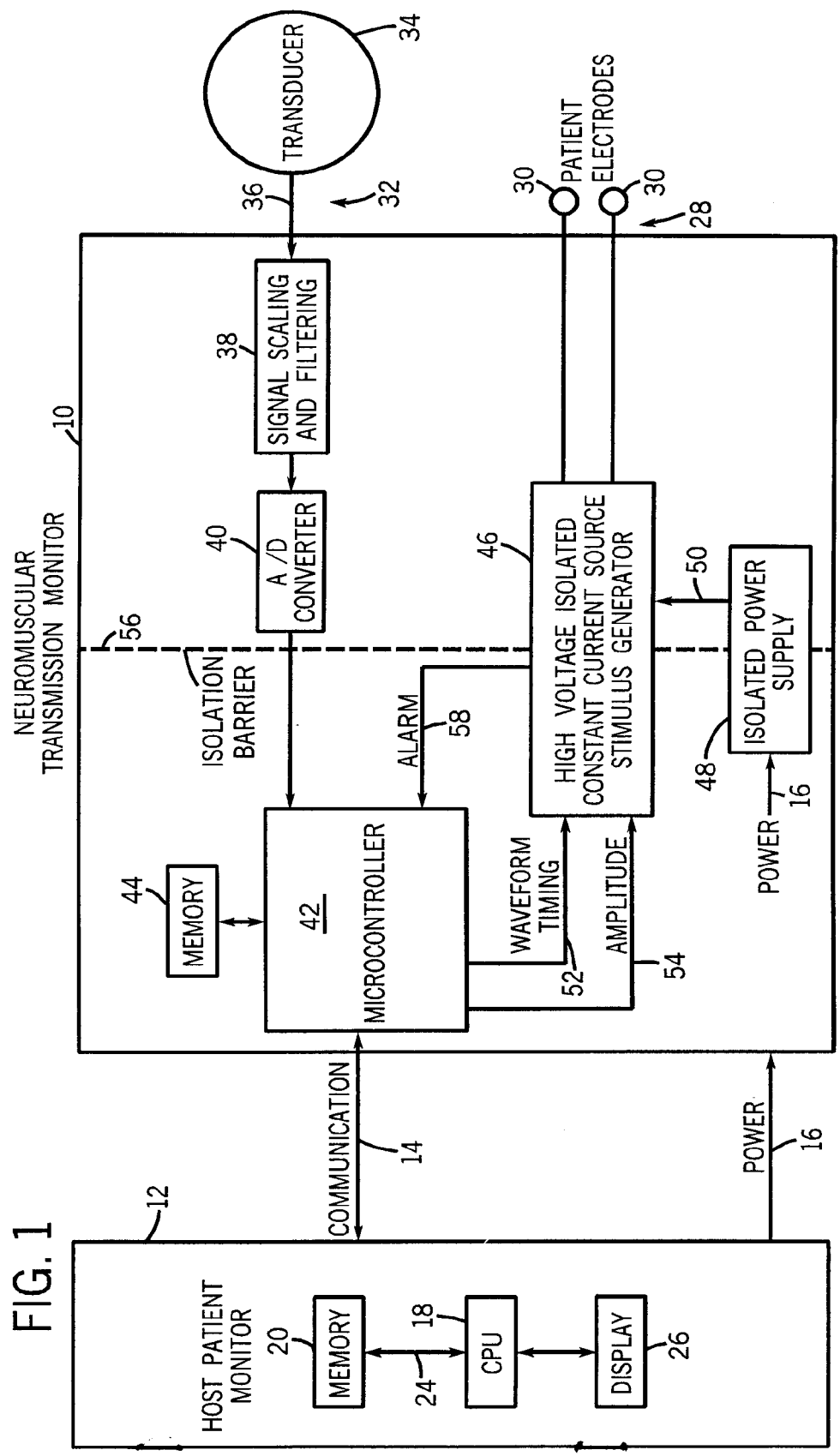
FIG. 1 is a block diagram of a neuromuscular transmission monitor and host patient monitor, incorporating the present invention.

Referring to FIG. 1, a neuromuscular transmission monitor 10, in accordance with the present invention, is connected to a host monitor 12 through a communications link 14. Typically, the neuromuscular transmission monitor 10 receives power 14 via the host monitor 12. Among other things, the host monitor 12 includes a central processing unit 18 connected to a memory unit 20 via a data link 24. The memory unit 20 may. be RAM, ROM, a mass storage unit, a floppy disk, or any other computer readable storage medium, or a combination thereof. The CPU 18 processes data, in accordance with the present invention, and is connected to a display 26 for output to an operator.

The neuromuscular transmission monitor 10 has at least one output 28, but preferably a plurality of outputs, connected to a plurality of patient electrodes 30 to stimulate a selected muscle, or muscles, of a patient under anesthesia care. The neuromuscular transmission monitor 10 has at least one input 32 connected to a transducer 34, such as an accelerometer, strain gage, piezo film, etc., which are used to quantify the degree of muscle movement and capable of sensing neuromuscular activity of a patient. The transducer 34 is a pressure sensitive transducer and measures the neuromuscular response to the muscle stimuli introduced by the patient electrodes 30 and creates a neuromuscular response signal 36 responsive to the muscle stimuli. The neuromuscular transmission monitor 10 receives the neuromuscular response signal 36 into a signal scaling and filtering circuit 38. After scaling the signal and filtering noise, the signal is converted from an analog signal to a digital signal in A/D converter 40 and is sent to a microcontroller 42 for processing. The microcontroller 42, or processing unit, is connected to a memory 44, much like memory 20, or any other computer readable storage medium, but in a preferred embodiment, is a combination of ROM and RAM.

A power supply 48 creates an isolated power supply 50 to a stimulus generator 46. The microcontroller 42 is connected to the stimulus generator 46 to control power to the patient electrodes 30. The stimulus generator 46 receives a waveform timing signal 52 and an amplitude control signal 54 from the microcontroller 42 and creates a constant current source that is isolated from the high voltage power source 16. This high voltage isolated constant current source stimulus generator 46 provides a stimulus waveform and current depending on the stimulus mode selected and the resulting waveform timing and amplitude control signals 52, 54. The neuromuscular transmission monitor 10 is electrically isolated from line voltage and other patient connections schematically shown by isolation barrier 56. Such electrical isolation is typically provided by a medical grade isolation transformer. Additionally, the electrode outputs are typically isolated from the line and other components of the system as well.

If a compliance voltage threshold is exceeded, an alarm signal 58 is generated by the stimulus generator 46 and supply to the microcontroller 42. Also, if the system is unable to deliver a specified current, for example due to high skin impedance or lead failure, the stimulus generator 46 produces an alarm signal 58 that is discernable by the microcontroller 42. Preferably, the microcontroller is connected to a warning light (not shown) that may either be a component of the host monitor 12, the neuromuscular transmission monitor 10, or a stand-alone device that will light responsive to the alarm signal 58.

The measurement of neuromuscular transmission has a wide dynamic range and the complete spectrum is typically comprised of three segments each having a unique scale and parameter definition. These three stimulus modes include a first, least sensitive stimulus mode for partial neuromuscular blocking, which is commonly referred to as the Train-of-Four (TOF) ratio. The TOF method relies on a principle referred to as "fade." Since there is a finite supply of the neurotransmitter acetylcholine (ACh), a rapid series of several stimuli (e.g., a "train-of-four" stimuli pulses), results in a "fade" of the neuromuscular response. Since ACh cannot be produced as rapidly as it is used, subsequent stimuli release less and less ACh. The constant number of blocking drug molecules can then compete more successfully with the ACh molecules for receptor sites. The first pulse of the TOF response is unaffected by fade, or ACh reserves, while the second, third, and fourth pulses are applied so rapidly that the production of ACh cannot meet the demand. The blocking drug therefore becomes more and more effective in competing with the ACh for receptor sites and the amplitudes of the succeeding pulses are reduced. Preferably, the TOF method applies four 200 ms. constant current stimuli in 0.5 seconds. The ratio of the last response pulse amplitude divided by the first response pulse amplitude is used to compute the "TOF ratio." This ratio effectively cancels any irregularities in absolute amplitude due to position or temperature changes. A TOF ratio of 1.0 indicates no neuromuscular block is present, while a TOF ratio of 0.7 is generally considered the minimum value for removing a patient from a ventilator.

A second, intermediate stimulus mode for moderate neuromuscular blocking (i.e., a medium sensitivity segment) is known as the Twitch Count (TC) which is generally used when there is a moderate degree of paralyzation. The Twitch Count is the number of responses received in response to a series of constant current pulses. A Twitch Count scale typically ranges from 1 to 3 or 1 to 4. A TC value of 4 represents 4 neuromuscular responses that result from 4 constant current pulses. It is generally believed that if a TC of 4 is achieved, the amount of blocking is likely light enough to obtain a TOF ratio. Therefore, in accordance with a preferred embodiment of the invention, a maximum TC count of 3 will be assumed for this second, intermediate stimulus mode.

A third, most sensitive, stimulus mode is used for heavy neuromuscular blocking where a high amountn of muscle relaxant is used. This third mode is known as the Post Tetanic Count(PTC). A PTC value can vary from 0 to 20, or in some cases, 0 to 15. The preferred embodiment utilizes a PTC variance of 0 to 15. However, one skilled in the art will readily recognize that if a higher resolution is sought, a PTC of 0 to 20 may be utilized. The PTC value is acquired by first applying a high frequency stimulus to sensitize the muscle at approximately 50 Hz. Afterwards, a series of 1 Hz pulses are applied and the PTC value is the number of responses acquired after the lower frequency pulses are applied. Another form of the PTC mode includes a "pre-tetanic" 1 Hz single twitch stimulus applied for 30 seconds, followed by the 50 Hz tetanic stimulation for 5 seconds. After a 3-second pause, the 1 Hz single twitch stimulus is applied for 15 seconds, by which time the response of the post-tetanic single switch stimulus is captured.

A fourth, rarely used stimulus mode, and scale, can include a Rapid Normalized Twitch Amplitude (RNTA) mode. The RNTA is used occasionally in critical situations. The RNTA measures the amplitude rapidly, typically at 1 second intervals, to determine when intubation is possible in an emergency setting. Other even less frequently used forms of stimulation include a Double Burst Stimulation (DBS), a single twitch and single tetanic methods. One skilled in the art will recognize that these methods may be incorporated into the present invention as well, however, their declining use indicates a lower likelihood of need for utilizing these methods.

As will now be appreciated by those skilled in the art, such multiple, unique scales and parameter definitions, each used for essentially the same purpose (i.e., to measure neuromuscular transmission), can lead to confusion. In accordance with one aspect of the present invention, a computer program is disclosed that resides on a computer readable memory 20, 44, that is capable of causing a processor, 18, 42, when executed, to receive a neuromuscular response value that is in one of at least 2 different formats, then determine which one of the at least 2 different formats the neuromuscular response value is in, and then convert the neuromuscular response value to a universal value applicable to a single scale that encompasses each of the different formats.

The program includes a memory 20, 44 having stored thereon a look-up table (Table 1) used by the processor 18, 42 to convert the neuromuscular response value. In a preferred embodiment, the look-up table includes conversion data for the TOF ratio format, the PTC value format, and the TC value format. The look-up table may also include conversion data for a normalized twitch amplitude, single tetanic, and double burst stimulation (DBS) measurements. In accordance with one aspect of the invention, the computer program resides in memory 44 of the neuromuscular transmission monitor 10. In this embodiment, the host monitor 12 simply initiates a command to begin neuromuscular transmission monitoring, and then the neuromuscular transmission monitor 10 receives the data value, determines the correct mode, converts the results to a new simplified scale, and reports the results to the host monitor 12. Alternatively, the computer program may reside in memory 20 of the host monitor 12 which is connected to receive data from the neuromuscular transmission monitor 10. In this second scenario, the neuromuscular transmission monitor 10 is less autonomous and receives detailed commands to supply a certain stimulus and receive data in response from the host monitor 12. In this case, the computer program that resides in memory 20 is executed and run by CPU 18 in host monitor 12.

Figure 2:
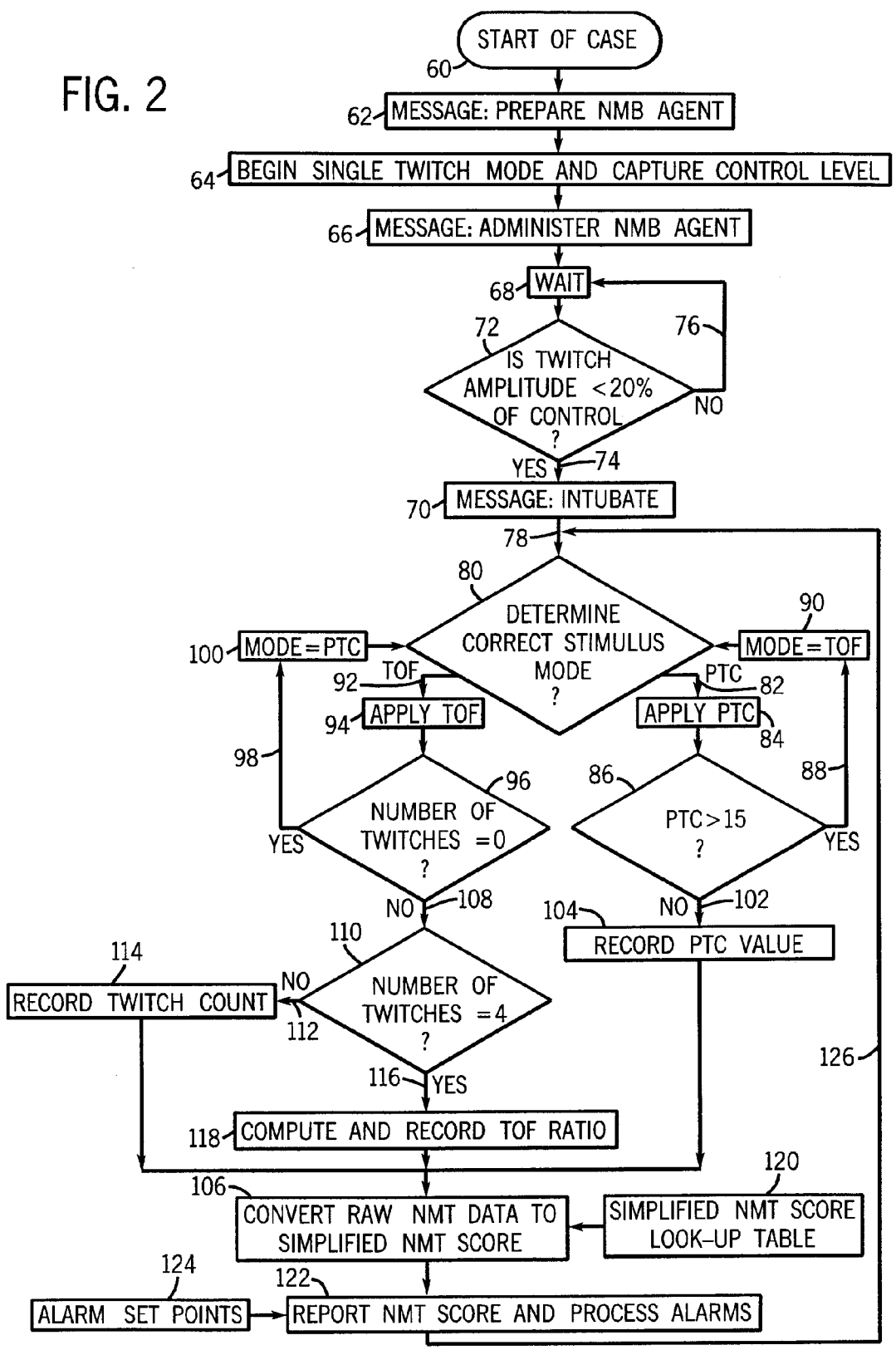
FIG. 2 is a flow chart depicting an algorithm and the method that are implemented in the apparatus of FIG. 1.

Referring now to FIG. 2, an algorithm is disclosed in accordance with the present invention. Upon initialization 60, the start of neuromuscular transmission monitoring of a non-emergency case begins with displaying a message to prepare the neuromuscular blocking (NMB) agent 62. The capture control level of the neuromuscular transmission monitor 10 is then set and the single switch mode is begun at 64. The NMB agent is then administered to the patient at 66 and after a predetermined time 68, the patient is intubated at 70 if the twitch amplitude is less than 20% of the control level 72, 74. Otherwise 76, the NMB agent is given more time to take effect 68. In some cases, the patient may have already been intubated for example, if the patient was given emergency care. In those cases, the algorithm would have a jump around, or bypass from the start of the case 60 to just past the instruction to intubate 70.

After the patient is intubated 70, 78, the system makes an initial determination as to the correct status mode 80. This step may be done automatically or manually, depending on the clinician's desires. If done manually, there is no question as to the correct stimulus mode. However, if done automatically, based on the values read, the system may reset itself after looping for several cycles. That is, suppose that the initial determination selects the PTC stimulus mode 82, and after the PTC stimulus mode is applied 84, if the PTC is greater than the value 15, at 86, 88, the system resets the stimulus mode to the TOF ratio mode 90. Conversely, if the TOF ratio mode is initially selected 92, and applied 94, if the number of twitches of the Twitch Count (TC) is zero, at 96, 98, the mode is switched to PTC at 100. However, in the automatic mode, the default selection is to start with the least aggressive stimulus. That is, the system would start with the TOF mode and if four twitches are indicated the TOF mode is selected. If one, two, or three twitches are indicated, the Twitch Count mode is selected. If no twitch responses are indicated, the PTC mode is selected.

If the PTC value is 15 or less at 86, 102 the PTC value is recorded at 104 and the algorithm proceeds to the conversion step 106. On the other hand, if in the TOF ratio mode 92, 94, and the number of twitches is more than zero at 96, 108, and if the total number of twitches does not equal four at 110, 112, the Twitch Count is recorded at 114, and the algorithm proceeds to the conversion step 106. In this case, there was not enough twitches to acquire a TOF ratio. However, if there are 4 twitches 110, 116, the TOF ratio is then computed and recorded at 118 and the algorithm proceeds to the conversion step at 106. In this manner, both the TOF ratio mode and the TC mode are accomplished through a single branch off the stimulus mode determination query 80. Once in the conversion step 106, the raw mode-specific value, which is unique to the particular mode of operation, is converted to a non-mode specific value using a look-up table 120, an example of which is shown below as Table 1.

TABLE 1

| Stimulus Mode | Conventional Scale | NMUS Scale |
|---|---|---|
| T O F Ratio | 100% | 10 |
| T O F Ratio | 90% | 10 |
| T O F Ratio | 80% | 9 |
| T O F Ratio | 70% | 9 |
| T O F Ratio | 60% | 8 |
| T O F Ratio | 50% | 8 |
| T O F Ratio | 40% | 8 |
| T O F Ratio | 30% | 7 |
| T 0 F Ratio | 20% | 7 |
| T O F Ratio | 10% | 7 |
| Twitch Count | 3 | 6 |
| Twitch Count | 2 | 5 |
| Twitch Count | 1 | 4 |
| P T C | 15 | 3 |
| P T C | 10 | 2 |
| P T C | 5 | 1 |
| P T C | 0 | 0 |

The simplified score is then reported and/or displayed at 122 and the alarms are processed based on predetermined alarm set points 124. The algorithm can then continue to reiterate 126 until the clinician determines extubation can be conducted safely based on the simplified score and the clinician's experience.

As will now be evident, Table 1 shows a simplified, single progressive scale that encompasses at least the three major stimulus modes. Table 1 shows for each stimulus mode, the range in the conventional scale and its corresponding Neuromuscular Universal Score (NMUS) on the NMUS scale. This single, progressive universal scale is not only easy to learn and use, a trend display using this new score is readily comprehensible since the score is progressive from maximum blocking to minimum blocking or vice versa. The scale can be expanded or contracted further. For example, a $4^{th}$ twitch count could be added as well as a 5th PTC score of 20. Conversely, every other TOF ratio could be eliminated or combined for reduced resolution. Table 1 shows the current preferred embodiment.

Accordingly, the present invention includes a method of neuromuscular transmission scoring that includes the steps of applying a neuromuscular stimuli to a patient, measuring a neuromuscular response from the patient, and assigning a universal value of the neuromuscular response to a single progressive scale that encompasses at least two stimulus modes, each stimulus mode having a unique scale and parameter definition.

In the preferred embodiment, the method includes a single progressive scale that includes at least three stimulus modes, a first least sensitive stimulus mode for partial neuromuscular blocking, a second intermediate stimulus mode for moderate neuromuscular blocking; and a third most sensitive stimulus mode for heavy neuromuscular blocking. The method further includes determining which stimulus mode is correct of the three stimulus modes for a particular neuromuscular response, determining a conventional value of the particular neuromuscular response based on a scale for the determined stimulus mode, and then converting the first value to the universal value. The unique scales and parameters include a ratio of a last neuromuscular response divided by a first neuromuscular response ranging from 0 to 100%, a Twitch Count ranging from 1 up to 4, and a Post-Tetanic Count value ranging from 0 up to 20.

The invention also includes a method of converting multiple NT measurement scores to a single progressive scale including applying a neuromuscular stimuli to a patient, measuring a neuromuscular response of the patient, and determining which one of at least two different scales the neuromuscular response belongs in, and then assigning a value of the neuromuscular response within the one of the at least two different scales. The assigned value is then converted to a single progressive scale encompassing each of the at least two different scales. The method includes displaying the converted assigned value to a clinician for further evaluation. The scales may include a TOF ratio scale, a Post-Tetanic Count scale, and a Twitch Count scale.

The invention includes a neuromuscular transmission monitor (NTM) that includes at least one patient electrode to stimulate a muscle of a patient and a transducer to measure a neuromuscular response to the muscle stimuli and create a neuromuscular response signal therefrom. A power supply is connected to the patient electrode to supply muscle stimulating power to the patient electrode. A processing unit is supplied and connected to the patient electrode and the transducer to control the muscle stimulating power to the patient electrode. The processing unit processes the neuromuscular response signal from the transducer and is programmed to determine a correct stimulus mode for the neuromuscular response signal and produce a non-mode specific value applicable to a single scale that encompasses multiple stimulus modes based on the determined stimulus mode and the neuromuscular response signal.

The act of producing a non-mode specific value is further defined to first assign a mode-specific value for the neuromuscular response signal based on the determined stimulus mode and the neuromuscular response signal. Then, the processor is programmed to convert the mode specific value to a non-mode specific value of the single scale encompassing the multiple stimulus modes. A look-up table is provided having therein a non-mode specific value for each mode specific value. The processing unit converts the data by reading the non-mode specific value from the look-up table using the mode specific value. A display device is provided and connected to the processing unit to output the non-mode specific value to the clinician. The processing unit is further programmed to operate in a TOF ratio stimulus mode, a PTC stimulus mode, and a TC stimulus mode, as well as a Rapid Normalized Twitch Amplitude (RNTA) stimulus mode.

In an alternate embodiment, the monitor further includes a host monitor having a processing unit that is programmed to perform the determination and production steps such that the monitor acts as a slave to the host monitor.

The present invention has been described in terms of the preferred embodiment, and it is recognized that equivalents, alternatives, and modifications, aside from those expressly stated, are possible and within the scope of the appending claims.

What is claimed is:

1. A method of neuromuscular transmission scoring comprising the steps of:
applying a neuromuscular stimulus to a patient;
measuring a neuromuscular response from the patient;
assigning a universal value of the neuromuscular response to a single progressive scale that encompasses at least two stimulus modes, each stimulus mode having a unique scale and parameter definition.

2. The method of claim 1 wherein the single progressive scale is further defined to include at least a first, least sensitive stimulus mode for partial neuromuscular blocking; a second, intermediate stimulus mode for moderate neuromuscular blocking; and a third, most sensitive stimulus mode for deep neuromuscular blocking.

3. The method of claim 2 further comprising the steps of:
determining which stimulus mode is correct from three stimulus modes for a particular neuromuscular response;
determining a conventional value of the particular neuromuscular response based on a scale for the determined stimulus mode; and
converting the first value to the universal value.

4. The method of claim 1 wherein the single progressive scale is further defined to include at least three stimulus modes and further comprises the step of defining each unique scale and each parameter to include:
a ratio of a last neuromuscular response divided by a first neuromuscular response ranging from 0 up to 100%;
a twitch count ranging from 1 up to 4; and
a post tetanic count value ranging from 0 up to 20.

5. The method of claim 4 including a fourth stimulus mode comprising a rapid normalized twitch amplitude scale.

6. A computer program residing on computer readable memory capable of causing a processor, when executed, to:
receive a neuromuscular response value that is in one of at least two different formats;
determine which one of the at least two different formats the neuromuscular response value is in; and
convert the neuromuscular response value to a universal value applicable to a single scale encompassing each of the at least two different formats.

7. The computer program of claim 6 wherein the computer program resides in memory of a neuromuscular transmission monitor.

8. The computer program of claim 7 wherein the neuromuscular transmission monitor is connected to transmit and receive data to or from a host patient monitor.

9. The computer program of claim 6 wherein the computer program resides in memory of a host patient monitor connected to receive data from a neuromuscular transmission monitor.

10. The computer program of claim 6 further comprising a memory having stored thereon a look-up table used by the processor to convert the neuromuscular transmission response value.

11. The computer program of claim 10 wherein the look-up table includes conversion data for at least three different formats, including a TOF ratio format, a PTC value format, and a TC value format.

12. The computer program of claim 11 wherein the look-up table further includes conversion data for a normalized twitch amplitude format.

13. A method of converting multiple neuromuscular transmission measurement scales to a single progressive scale comprising the steps of:
applying a neuromuscular stimuli to a patient;
measuring a neuromuscular response of the patient;
selecting which scale of at least two different scales the neuromuscular response belongs therein;
assigning a value of the neuromuscular response within the selected scale of the at least two different scales;
converting the assigned value to a single progressive scale encompassing each of the at least two different scales.

14. The method of claim 13 further comprising the step of displaying the converted assigned value to a clinician.

15. The method of claim 13 wherein the two different scales include a TOF ratio and a post tetanic count.

16. The method of claim 15 further including a third scale comprising a twitch count.

17. The method of claim 16 further including a fourth scale comprising a rapid normalized twitch amplitude scale.

18. The method of claim 13 further comprising the steps of defining three different scales for the neuromuscular response that include:
a ratio of a last neuromuscular response divided by a first neuromuscular response ranging from 0 up to 100%;
a twitch count ranging from 1 up to 4; and
a post tetanic count value ranging from 0 up to 20.

19. The method of claim 18 wherein the step of converting utilizes a look-up table based on which scale and the value assigned in the scale.

20. A neuromuscular transmission monitor comprising:
a patient electrode to stimulate a muscle of a patient;
a power supply connected to the patient electrode to supply muscle stimulating power to the patient electrode;
a transducer to measure a neuromuscular response to the muscle stimuli and create a neuromuscular response signal therefrom;
a processing unit connected to the patient electrode and the transducer to control the muscle stimulating power to the patient electrode and process the neuromuscular response signal from the transducer, and programmed to:
determine a correct stimulus mode for the neuromuscular response signal; and
produce a non-mode specific value applicable to a single scale that encompasses multiple stimulus modes based on the determined stimulus mode and the neuromuscular response signal.

21. The neuromuscular transmission monitor of claim 20 wherein the act to produce a non-mode specific value is further defined to:
assign a mode-specific value for the neuromuscular response signal based on the determined stimulus mode and the neuromuscular response signal; and
convert the mode-specific value to a non-mode specific value of the single scale encompassing multiple stimulus modes.

22. The neuromuscular transmission monitor of claim 21 further comprising a look-up table having therein a non-mode specific value for each mode specific value, and wherein the processing unit's convert act includes reading the non-mode specific value from the look-up table using the mode-specific value.

23. The neuromuscular transmission monitor of claim 20 further comprising a display device connected to the processing unit to output the non-mode specific value.

24. The neuromuscular transmission monitor of claim 20 wherein the processing unit is further programmed to operate in a TOF ratio stimulus mode, a PTC stimulus mode, and a TC stimulus mode.

25. The neuromuscular transmission monitor of claim 20 further comprising a host monitor having a processing unit programmed to perform the determination and production acts.

26. The neuromuscular transmission monitor of claim 24 wherein the processing unit is further programmed to operate in a RNTA stimulus mode.

27. The neuromuscular transmission monitor of claim 20 wherein processing unit is further programmed to convert three different scales, one for each stimulus mode, to the single scale, three different scales include at least:

a ratio of at last neuromuscular response divided by a first neuromuscular response ranging from 0 up to 100%, a twitch count ranging from 1 up to 4; and a post tetanic count value ranging from 0 up to 20.

* * * * *